United States Patent [19]

Baird et al.

[11] Patent Number: 5,300,429
[45] Date of Patent: Apr. 5, 1994

[54] PHB-FREE GELLAN GUM BROTH

[75] Inventors: John K. Baird; Joseph M. Cleary, both of San Diego, Calif.

[73] Assignee: Merck & Co., Inc., Rahway, N.J.

[21] Appl. No.: 21,635

[22] Filed: Feb. 22, 1993

Related U.S. Application Data

[63] Continuation of Ser. No. 839,723, Feb. 18, 1992, abandoned, which is a continuation of Ser. No. 571,397, Aug. 23, 1990, abandoned.

[51] Int. Cl.$^5$ ............................................. C12P 19/04
[52] U.S. Cl. ..................................... 435/101; 435/104; 435/253.6; 435/832; 536/123; 536/114
[58] Field of Search ...................... 435/101, 104, 253.6, 435/832; 536/123, 114

[56] References Cited

U.S. PATENT DOCUMENTS

| | | | |
|---|---|---|---|
| 4,296,203 | 10/1981 | Wernau | 435/104 |
| 4,326,052 | 4/1982 | Kang et al. | 536/1.1 |
| 4,326,053 | 4/1982 | Kang et al. | 536/1.1 |
| 4,377,636 | 3/1983 | Kang et al. | 435/101 |
| 4,385,123 | 5/1983 | Kang et al. | 435/253 |
| 4,385,126 | 5/1983 | Chen et al. | 436/518 |
| 4,503,084 | 3/1985 | Baird et al. | 426/573 |

FOREIGN PATENT DOCUMENTS 12552 of 1980 European Pat. Off. .

OTHER PUBLICATIONS

Williamson et al. J. Gen. Microbiol. 19, 196–209 (1958).
Moorhouse et al. Solution Properties of Polysaccharies Chapter 9 pp. 111–124.
Kang et al. Applied & Environmental Microbiology, vol. 43, No. 5 May 1982, pp. 1086–1091.

Primary Examiner—Johnnie R. Brown
Assistant Examiner—Pamela S. Webber
Attorney, Agent, or Firm—Richard S. Parr; Melvin Winokur; Hesna J. Pfeiffer

[57] ABSTRACT

*P. elodea* mutants are produced which produce gellan gum broth which contains no detectable amount of poly-$\beta$-hydroxy-butyrate (PHB).

3 Claims, No Drawings

PHB-FREE GELLAN GUM BROTH

This is a continuation of application Ser. No. 07/839,723 filed Feb. 18, 1992, which is a continuation of Ser. No. 07/571,397 filed Aug. 23, 1990, both now abandoned.

BACKGROUND OF THE INVENTION

Gellan gum, also known as S-60, is a bacterial heteropolysaccharide produced by aerobic fermentation of suitable carbon and nitrogen sources in the presence of appropriate nutrients by the organism *Pseudomonas elodea*, ATCC 31461. Native gellan gum is described in U.S. Pat. No. 4,326,053. The term "gellan gum" includes the native (i.e., non-deacylated), deacylated, partially deacylated, and clarified forms thereof.

Processes for producing gellan gum are also described in U.S. Pat. Nos. 4,326,052; 4,377,636; 4,385,126 and 4,503,084.

When gellan gum is produced via these known processes, the resulting fermentation broth contains large amounts of the bacterial metabolite poly-$\beta$-hydroxybutyrate, an intracellular energy storage product. Based on dry weight of the total recovered biomass, PHB is present in amounts of about 15-25%.

SUMMARY OF THE INVENTION

*P. elodea* mutants have now been isolated which produce gellan gum broth containing no detectable amounts of PHB.

DETAILED DESCRIPTION OF THE INVENTION

As described above, gellan gum produced by known processes contains about 15-25% PHB. As a major insoluble impurity, this PHB is a significant contributor to the turbidity exhibited by reconstituted gellan gum solutions. Where a clarified product is desired, the PHB is a deterrent to facile clarification processes. Also, the synthesis of PHB represents an alternate biosynthetic pathway for the metabolism of the fermentation carbon source, and PHB production is favored by the high carbon, low nitrogen conditions which also favor synthesis of gellan polysaccharide. Consequently, the isolation of a mutant which does not produce PHB provides the potential for a more economic utilization of the carbon source which may be manifested by increased yield or conversion into gellan gum. Thus, the mutants of the present invention produce a PHB-free fermentation broth which contains substantially fewer insolubles than known broths and which can be purified by much simpler processes than the known processes. As an example, U.S. Pat. No. 4,326,052 teaches high temperature centrifugation of a low concentration (1%) gum solution, followed by millipore filtration to produce a clarified product. The fermentation broth of the present invention, advantageously, can be clarified by chemical and/or enzyme treatment of the broth (or of a reconstituted solution), as opposed to filtration to remove insoluble materials. Even without a specific clarification step, the present broth would nevertheless produce a purer product with less insoluble material due to the absence of PHB.

From the broths of this invention can be produced the gellan gum forms known in the prior art, i.e., non-deacetylated, deacylated, etc. These gums would have the same utilities as the known gums.

The mutation of *P. elodea* to a form which produces PHB-free broth is carried out using well-established mutagens and techniques. Particular reference is made to the alkylating agents EMS (ethylmethane sulfonate), MMS (methylmethane sulfonate), and DES (diethyl sulfonate) and to the mutagen NG (N-methyl-N'-nitro-N-nitrosoguanadine) and also to the techniques described in J. H. Miller, *Experiments in Molecular Genetics*, Cold Spring Harbor Laboratory (1972).

Using such techniques, *P. elodea* is exposed to a mutagen such as NG according to the methods of Miller, supra, and the culture plated out on YM agar medium (Cadmus, M. C., et al., *Can. J. Microbiol.*, 22, 942-948 (1976)). After incubation for 48 to 72 hours, individual colonies are removed and analyzed directly for the absence of PHB as by the method of D. H. Williamson et al., J. Gen. Microbiol 19, 196-209 (1958). Alternatively, colonies are selected and cultured in YM liquid medium. After culturing for 24 to 48 hours, an aliquot of the culture broth is analyzed for PHB by the method above.

Those mutant strains which produce diminished amounts of PHB while still producing gellan gum are retained. The procedure is iterated until no PHB is detected in the broth.

An embodiment of this invention is a biologically pure culture of a *P. elodea* mutant which produces fermentation broth containing recoverable amounts of gellan gum by submerged, aerobic fermentation of an assimilable carbon source but containing no detectable amounts of PHB. (i.e., no more than 0.019% (w/v)).

A preferred such mutant, designated LPG-2, is another embodiment of the invention. An LPG-2 culture has been deposited with the ATCC under the terms of the Budapest Treaty on Nov. 16, 1989, and given accession no. 53967. Under the terms of the agreement with the ATCC, this strain will be maintained for a period of at least 30 years from said deposit date.

Another embodiment is any progeny of ATCC 53967.

Another embodiment is a process for preparing fermentation broth containing recoverable amounts of gellan gum but no detectable amounts of PHB, which comprises growing a *P. elodea*. mutant as described above by submerged, aerobic fermentation of an assimilable carbon source.

Another embodiment is said fermentation broth.

The invention is further defined by reference to the following examples, which are intended to be illustrative and not limiting. Temperatures are in degrees Celsius (°C).

In some of the data presented, levels of PHB are shown comparing wild type *P. elodea* to LPG-2. In these data there are shown PHB levels for LPG-2 which are very small but greater than 0%. These values are not the result of actual detectable PHB content but rather of "background noise," i.e., lack of complete specificity of the turbidity test method. To determine actual detectable PHB content, wild type and LPB-2 broths were compared by the more specific and sensitive test method of Law et al., *J. Bact.*, 82, pp 33-36 (1961). This method involves conversion of PHB to crotonic acid by digestion with concentrated $H_2SO_4$. The digested material was then scanned by UV light in the range 220-400 nm. Although the LPG-2 broths showed a detectable amount of turbidity (albeit much less than wild type broths) throughout the range, they showed no maxima at 235 nm. Crotonic acid has a specific absorbance at 235 nm. The absence of a peak at this wavelength indicates the lack of crotonic acid and, therefore, the lack of any detectable precursor PHB.

EXAMPLE 1

Wild Type vs. LPG-2 PHB Content

*P. elodea* wild type and LPG-2 strains were grown up under several different conditions, and the PHB contents of the resultant broths determined.

Broth strains were grown on YM ® agar plates from lyophilized samples.

After 48-72 hours of incubation on the fresh plates, a loopful of culture was used to inoculate a 500 ml Erlenmeyer shake flask containing 100 ml of Stage 1 seed medium. This was incubated on a shaker for 20-26 hours, then 2-6% of the Stage 1 medium was used to inoculate a 2-liter shake flask stage 2 seed medium. This was allowed to incubate for 20-26 hours prior to Stage 3 seed fermentation.

The incubation temperature for Stages 1 and 2 was 36° C.

| Constituent | Stage 1 | Stage 2 |
|---|---|---|
| Yeast Extract | 3 g/L | — |
| Malt Extract | 3 g/L | — |
| Peptone | 5 g/L | — |
| Dextrose | 10 g/L | — |
| Water Source | Deionized | Tap |
| $K_2HPO_4$ | — | 2.00 g/L |
| $KH_2PO_4$ | — | 1.00 g/L |
| $MgSO_4.7H_2O$ | — | 0.10 g/L |
| $NaNO_3$ | — | 1.90 g/L |
| Promosoy[1] | — | 0.50 g/L |
| $FeSO_4 7H_2O$ | — | 5.0 mg/L |
| $CoCl_2 6H_2O$ | — | 0.024 mg/L |
| 43/42 Corn Syrup | — | 37.5 g/L |
| Hodag K-60[2] | — | — |

[1]Soy protein concentrate, Central Soya, Chemergy Div.
[2]Defoamer (mixture of esters), Hodag Chem. Corp.

The Stage 3 seed fermentation used an 0.09% inoculation from the Stage 2 fermentation and the following medium:

| Constituent | Concentration | |
|---|---|---|
| Corn Syrup | 30 g/L | (solids) |
| $K_2HPO_4$ | 2 g/L | |
| $KH_2PO_4$ | 1 g/L | |
| $NH_4NO_3$ | 0.9 g/L | (autoclave separately) |
| Promosoy | 0.5 g/L | |
| $MgSO_4.7H_2O$ | 0.1 g/L | |
| $FeSO_4.7H_2O$ | 5 ppm | |
| Ho-Le Salts[1] | 0.1% | (1 ml/L) |
| K-60 Hodag | 0.031% | |

1. Ho-Le Salts formulation:

| Constituent | mg/L Stock | Constituent | mg/L Stock |
|---|---|---|---|
| $H_3BO_3$ | 285 | Na-tartrate | 2098.0 |
| $MnCl_2.4H_2O$ | 1800 | $ZnCl_2$ | 20.8 |
| $FeSO_4.7H_2O$ | 2487.2 | $CoCl_2.6H_2O$ | 40.4 |
| $CuCl_2$ | 26.9 | $MgMoO_4$ | 19.2 |

The Stage 3 fermentation was run for 20-24 hours, prior to inoculation for the final fermentation stage.

For the final fermentation, 600 ml of the Stage 3 fermentation broth was used to inoculate 9400 mL of medium in a 14 L fermentor. The following basal fermentation medium was used:

| Constituent | Concentration |
|---|---|
| Corn Syrup | 30 g/L (solids) |
| $K_2HPO_4$ | 5 g/L |
| $MgSO_4.7H_2O$ | 0.1 g/L |
| Promosoy | 1.15 g/L |
| $FeSO_4.7H_2O$ | 5 ppm |
| Ho-Le Salts | 0.1% (1 ml/L) |
| Hodag K-60 | 094% |

The pH of the fermentor was automatically controlled at 6.5. At the end of the fermentation (48-96 hrs.), the broths were analyzed by the turbidimetric and crotonoic acid methods. The crotonoic acid method showed no crotonoic acid and, therefore, no precursor PHB.

Two different media sources of nitrate were used. Medium A utilized 0.19% (wt/wt) of $NaNO_3$. Medium B utilized 0.09% (wt/wt) of $NH_4NO_3$. The fermentations were also varied in temperature (30° and 36° C.) and water (tap and de-ionized), as shown in Table 1—1. By this combination of variables, eight different fermentation conditions were used for each strain of *P. elodea*. From these data it was concluded that the conditions of choice for LPG-2 are sodium nitrate in DI water at 36° C.

TABLE 1-1

LPG-2 vs WT

| Trial | Strain | Med./T/$H_2O$) | Broth PHB % (w/v) | Dry Gum % Purity |
|---|---|---|---|---|
| 4 | LPG-2 | A/30/tap | 0.015 | 86.0 |
| 12 | LPG-2 | A/30/DI | 0.015 | 90.3 |
| 8 | LPG-2 | A/36/tap | 0.006 | 77.9 |
| 16 | LPG-2 | A/36/DI | 0.004 | 90.0 |
| 2 | LPG-2 | B/30/tap | 0.012 | 86.1 |
| 10 | LPG-2 | B/30/DI | 0.017 | 88.8 |
| 6 | LPG-2 | B/36/tap | 0.019 | 84.7 |
| 14 | LPG-2 | B/36/DI | 0.007 | 90.0 |
| 3 | WT | A/30/tap | 0.318 | 63.1 |
| 11 | WT | A/30/DI | 0.368 | 66.2 |
| 7 | WT | A/36/tap | 0.369 | 61.7 |
| 15 | WT | A/36/DI | 0.330 | 66.5 |
| 1 | WT | B/30/tap | 0.224 | 68.2 |
| 9 | WT | B/30/DI | 0.260 | 72.8 |
| 5 | WT | B/36/tap | 0.203 | 68.7 |
| 13 | WT | B/36/DI | 0.342 | 63.7 |

The turbidimetric assay for PBH was developed from the method of D. H. Williamson and J. F. Wilkinson, Journal of General Microbiology, 19, 196-209, (1958). Samples were prepared by taking an aliquot of fermentation broth (0.1-0.5 ml), adding 10 vols. of a 5.25% sodium hypochlorite solution, mixing vigorously and incubating at 37° for 16 to 20 hrs. Turbidity of the resulting solution was determined at 600 nm on Gilford Model 250 spectrophotometer using a rapid sampler cuvette with a 1 cm pathlength. In Table 1—1, PHB is the calculated % PHB (w/v) in the fermentation broth and was determined by comparison with the turbidity of a purified PHB turbidimetric standard solution.

The PHB content of the broths was also determined by the method of Law and Slepecky, Journal of Bacteriology, 82, 33-36, (1961). Aliquots of broth (5 ml) were incubated with 5.75% sodium hypochlorite (5 ml) for 16 hrs at 37°. The insoluble residue was recovered by centrifugation, washed with water (5 ml) and resuspended in deionized water (5 ml). Aliquots (0.2 ml) were heated with concentrated sulfuric acid (4.8 ml) at 100° for 10 min. and the absorbance determined. In order to determine if the absorbance at 235 nm was due to crotonic acid or nonspecific absorbance, UV spectra were determined over the range of 220–400 nm. Samples from the WT broths gave a specific absorbance maximum at 235 nm, whereas samples from the LPG-2 broths did not. On this basis it was concluded that the LPG-2 broths did not contain any detectable amounts of PHB.

The fermentation product was recovered from the broth by adding 0.5 ml of 45% (w/v) potassium hydroxide per 100 gm of broth, by heating the broth at 121° (15 psi) for 15 min, adding 2 vol of isopropanol, separating and drying the precipitated fibers at 95° for 18 hr.

The gellan polysaccharide content of the recovered fermentation product was determined by the method of B. L. Browning, Methods of Wood Chemistry II, 632–633, (1967). A sample of the dried product was weighed, dissolved in water and decarboxylated with 19% hydrochloric acid. The liberated carbon dioxide was trapped in standard sodium hydroxide and the amount determined by back titration. In Table 1—1, the purity of the gellan product recovered from the fermentation of the LPG-2 strain is shown to be significantly higher than that from the WT strain under all fermentation conditions tested. % Purity was calculated by the formula:

$$\% \ CO_2 \cdot 684 \div 44$$

where 684 is the equivalent weight of deacylated gellan as the potassium salt and 44 is the molecular weight of $CO_2$.

% solids was determined by weighing a sample of the recovered product before and after drying to constant weight at 105°.

Purity data in Table 1—1 are expressed on a dry weight basis.

Deposit

*Pseudomonas elodea* LPG-2, deposited with the American Type Culture Collection, 12301 Parklawn Drive, Rockville, Md. 20852 USA, is designated ATCC 53967. The deposit was made Nov. 16, 1989 under the provisions of the Budapest Treaty on the International Recognition of the Deposit of Microorganisms for the Purposes of Patent Procedure and the Regulations thereunder (Budapest Treaty). Maintenance of a viable culture is assured for 30 years from the date of deposit. The organisms will be made available by ATCC under the terms of the Budapest Treaty, and subject to an agreement between Applicants and ATCC which assures unrestricted availability upon issuance of the pertinent U.S. patent. Availability of the deposited strains is not to be construed as a license to practice the invention in contravention rights granted under the authority of any government in accordance with its patent laws.

What is claimed is:

1. A biologically pure culture of Pseudomonas elodea strain LPG-2 having all of the identifying characteristics of ATCC 53967, said culture which produces broth containing recoverable amounts of gellan gum by submerged, aerobic fermentation of an assimilable carbon source wherein said gellan gum broth contains no more than 0.019% (w/v) of poly-$\beta$-hydroxy-butyrate, wherein the width of ATCC 53967 is between about 0.4–0.5 $\mu$m and the length is between about 1.5–2.5 $\mu$m.

2. A process for producing gellan gum broth containing recoverable amounts of gellan gum but no more than 0.019 (w/v) of poly-$\beta$-hydroxy-butyrate which comprises growing a biologically pure culture of Pseudomonas elodea strain LPG-2, having all of the identifying characteristics of ATCC 53967 in an aqueous nutrient medium by submerged aerobic fermentation of an assimilable carbon source, wherein the width of ATCC 53967 is between about 0.4–0.5 $\mu$m and the length is between about 1.5–2.5 $\mu$m, and recovering said gellan gum.

3. A fermentation broth produced by the process of claim 2 gellan gum but no more than 0.019% (w/v) of poly-$\beta$-hydroxy-butyrate.

* * * * *